United States Patent
Stridh et al.

(10) Patent No.: US 7,117,029 B2
(45) Date of Patent: Oct. 3, 2006

(54) METHOD OF AND APPARATUS FOR DERIVING INDICES CHARACTERIZING ATRIAL ARRHYTHMIAS

(75) Inventors: Martin Stridh, Lund (SE); Leif Sörnmo, Lund (SE)

(73) Assignee: Siemens Aktiengesellschaft, Munich (DE)

(*) Notice: Subject to any disclaimer, the term of this patent is extended or adjusted under 35 U.S.C. 154(b) by 446 days.

(21) Appl. No.: 10/260,838

(22) Filed: Sep. 30, 2002

(65) Prior Publication Data

US 2003/0069511 A1   Apr. 10, 2003

(30) Foreign Application Priority Data

Oct. 4, 2001   (SE)   ................................... 0103312

(51) Int. Cl.
  *A61B 5/04*   (2006.01)
(52) U.S. Cl. ...................... 600/515; 600/508
(58) Field of Classification Search ............... 600/515, 600/508, 509, 518, 519
  See application file for complete search history.

(56) References Cited

U.S. PATENT DOCUMENTS

| | | | |
|---|---|---|---|
| 4,680,708 A | * | 7/1987 | Ambos et al. ............... 600/509 |
| 5,046,504 A | * | 9/1991 | Albert et al. ................ 600/509 |
| 5,092,341 A | * | 3/1992 | Kelen ......................... 600/515 |
| 5,210,366 A | * | 5/1993 | Sykes, Jr. .................... 84/616 |
| 5,542,430 A | | 8/1996 | Farrugia et al. |
| 5,772,604 A | * | 6/1998 | Langberg et al. ........... 600/518 |
| 5,967,995 A | | 10/1999 | Shusterman et al. |
| 6,738,445 B1 | * | 5/2004 | Soulodre .................... 375/377 |

FOREIGN PATENT DOCUMENTS

| | | |
|---|---|---|
| EP | 0 862 928 | 9/1998 |
| EP | 1 112 757 | 7/2001 |
| EP | 1 123 716 | 8/2001 |
| WO | WO 00/69517 | 11/2000 |
| WO | WO 01/67950 | 9/2001 |

* cited by examiner

*Primary Examiner*—Robert E. Pezzuto
*Assistant Examiner*—Eric Bertram
(74) *Attorney, Agent, or Firm*—Schiff Hardin LLP

(57) ABSTRACT

In a method of and apparatus for deriving indices characterizing atrial arrhythmias, a temporally isolated portion of a digital representation of a time-domain electrical signal originating from the atria of a patient is frequency analyzed to provide a corresponding frequency spectrum. The obtained frequency spectrum is compared with a template frequency spectrum, selectively adapted dependent on previously obtained frequency spectra from different temporally isolated portions, to determine a frequency shift value and an amplitude value that optimize a correlation between the two spectra. An output representing the two determined values is used, possibly together with parameters describing the template frequency spectrum, to classify an atrial arrhythmia manifest in the digital representation.

7 Claims, 6 Drawing Sheets

METHOD OF AND APPARATUS FOR DERIVING INDICES CHARACTERIZING ATRIAL ARRHYTHMIAS

BACKGROUND OF THE INVENTION

1. Field of the Invention

The present invention relates to a method and apparatus for characterizing atrial arrhythmias and in particular to a method and apparatus employing time-frequency analysis of electrical signals originating from the atria in order to derive indicia for use in characterizing the arrhythmias.

2. Description of the Prior Art

It is desirable to find methods, particularly non-invasive methods, for the characterization and classification of atrial arrhythmias, including tachycardia, flutter and fibrillation. Information contained in the atrial activity must, in some suitable way, be quantified to accomplish this task. To date, the primary efforts in this field have been directed toward atrial fibrillation analysis although the same methods in many cases can be used for flutter and tachycardia. In the atrial fibrillation case, the atrial activity in an electrocardiogram (ECG), registered from either internal or external of the patient, has conventionally been classified by its maximum amplitude. The repetition rate (or atrial cycle length) of the f-waves in the ECG has also been investigated and serves as an index of the degree of atrial organization. Estimation of the average repetition rate can be based on spectral analysis. Such an approach gives a general picture of the signal by providing information about the average repetition rate by means of the peak location, the variation in the rate by the width of the peak and the average signal energy by the peak amplitude. This method is simple but provides valuable clinical information.

Atrial signals may be non-stationary but are repetitive and thus they can, during short intervals, be represented by a fundamental frequency signal, which reflects the repetition rate and a harmonic pattern which reflects the shape of the fibrillatory waveform. Based on this recognition a detailed feature extraction in the time-frequency plane for this type of signal may be achieved.

Time-frequency analysis (TFA) using an iterative cross-Wigner-Ville distribution (XWVD) to analyze the signals on a second-to-second basis is known and can provide a more detailed temporal characterization of variations in the repetition rate than the above mentioned approaches.

The XWVD models the frequency variations as a frequency-modulated sinusoid, which has a low-pass effect on the trends. Further, it only uses the energy in the fundamental frequency and is therefore not capable of tracking the shape of the signals as described by its harmonics. Another limitation is that, because of the large number of iterations performed, the computational complexity is relatively high.

SUMMARY OF THE INVENTION

This object is achieved in accordance with the present invention to provide a method, a computer program product and an apparatus for deriving indices that characterize atrial arrhythmias, wherein the aforementioned problems associated with known methods and systems are avoided, or at least alleviated.

This object is achieved in accordance with the present invention in a method for deriving within a digital data processing system, at least one index useful for characterizing atrial arrhythmias. This method employs a comparison between a frequency spectrum representative of a time-localized region of an input atrial electrical signal and a model or template frequency spectrum to provide values indicative of arrhythmia events. This reduces the number of iterative steps compared to the other computational analysis described above.

Preferably, the template frequency spectrum is adapted in a selective manner with each spectrum from different time localized regions. This has an advantage that the template spectrum can adapt to any changes in the waveform characteristics which occur over time and from patient to patient.

The adaptation may involve varying the frequency position of the fundamental peak of the template spectrum dependent on an averaged frequency spectrum obtained from the different time-localized regions of the input atrial signal. Tracking of the fundamental frequency peak in this manner reduces the computation necessary when calculating a frequency shift required to optimize the correlation between the template frequency spectrum and the frequency spectrum of the input atrial signal.

The set of indices obtained by the method according to the present invention can then serve as a basis for classification of atrial arrhythmias, for example by comparison within the digital data processing system of the obtained indices with those stored within a database of indices characterizing known arrhythmia types.

The above object also is achieved in accordance with the present invention in a computer program product which, when loaded into and executed by a digital signal processing system, causes the system to perform the inventive method described above.

The above object also is achieved in accordance with the present invention in an apparatus operating according to the inventive method described above.

DESCRIPTION OF THE PREFERRED EMBODIMENTS

Figure 1:
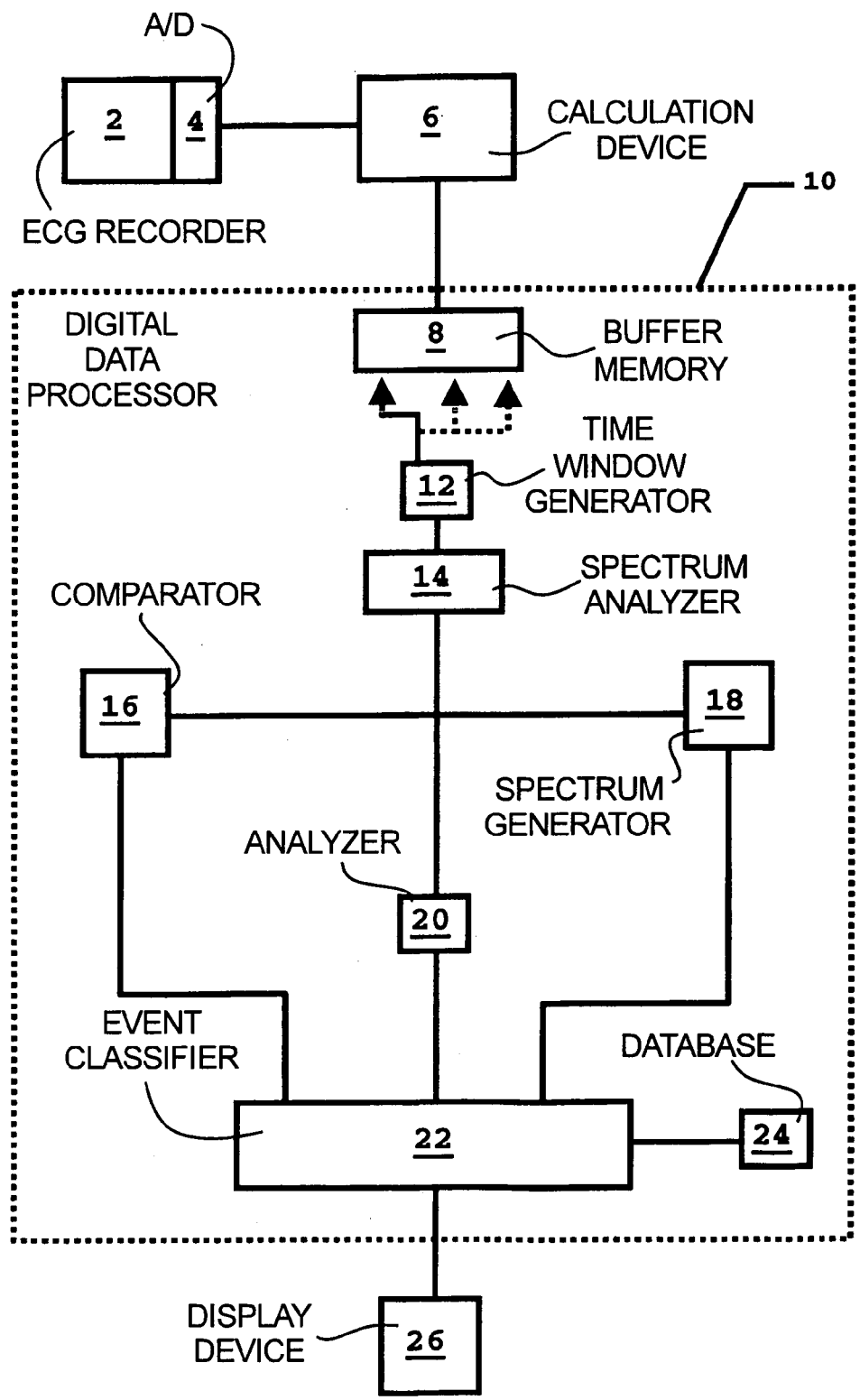
FIG. 1 shows an apparatus according to the present invention, configured to operate according to the method of the present invention.

Considering now the apparatus of FIG. 1, a conventional 12-lead surface ECG recorder 2 includes an analog to digital converter 4 which provides a digital output sampled at 1 kHz to a QRST cancellation device 6, such as the device described in U.S. Pat. No. 6,305,231. This device 6 is configured to provide an output down-sampled to 50 Hz, which is sufficient to describe a time-domain signal representing mainly the atrial activity of a patient's heart.

A buffer memory 8 of a digital data processor 10 is arranged to receive the down-sampled output from the QRST cancellation device 6. A time window generator 12 is configured to generate a variable location (illustrated by the broken arrows of FIG. 1) time window 12 to temporally isolate a portion of the data within the buffer memory 8 and provide it to spectrum analyzer 14 which operates to analyze the isolated portion of the time-domain signal into a frequency spectrum, $q_K$.

A comparator 16 is connected to a spectrum analyzer 14 to receive the analyzed frequency spectrum, $q_K$, and a template spectrum, $\phi$, from a spectrum generator 18 and is adapted to determine a frequency shift value, $\theta_k$, and amplitude value, $a_K$, required to optimize a correlation between the two types, as discussed in more detail below. The spectrum generator 18 is further configured to adapt the template spectrum, $\phi$, dependent on the frequency spectrum, $q_K$, of the input atrial signal in a manner described in more detail below.

An analyzer 20 is configured to parameterize the template spectrum, $\phi$, according to a descriptive model exemplified below to determine parameters useable as indices in the characterization of arrhythmia events which may be present in the atrial signal input into the digital signal processor 10.

An event classifier 22 is operably connected to the analyzer 20, to the comparator 16 and to a database 24 which holds parameter and value combinations and corresponding arrhythmia events. The event classifier 22 is configured to identify arrhythmia events present in the atrial signal input from the QRST cancellation device 6 after a comparison with the data stored in the database 24 and to output this identification, for example to a display device 26, such as a printer or visual display unit, to a data storage device (not shown), or for transmission to a remote client location.

It will be appreciated by those skilled in the art that a conventional microprocessor running a program code portion, originated using standard programming techniques, of a computer program product may be specifically adapted to perform the functions of the digital data processor 10. Such a microprocessor may be further programmed to perform the functions of the QRST cancellation device 6.

It will be further appreciated by those skilled in the art that the digital data processor 10 may be located remote of the surface ECG recorder 10 and may be employed to analyze ECG traces previously recorded and stored or to analyze in real time ECG traces communicated to the processor 10 via a telecommunications link such as an internet link.

The apparatus of FIG. 1 is configured to operate according to the method of the present invention by which characterization of atrial arrhythmias is based on a time-frequency distribution of an input atrial signal. Generally, the method involves construction of an initial template spectrum, $\phi_0$, as a single frequency peak at an initial fundamental frequency position, $p_0$, in a low amplitude noise floor. For a k:th signal block (time window) a corresponding frequency spectrum, $q_K$, is calculated and appended to a time-frequency distribution. A frequency shift, $\theta_k$, between the calculated spectrum, $q_K$, and the template spectrum, $\phi$, is determined by relatively frequency shifting one or other of them, preferably the template spectrum, $\phi$, to achieve a best match. An estimate of the amplitude, $a_K$, of the temporally isolated portion (k:th time window) of the input atrial signal is then made based on this frequency shift, $\theta_k$. Both the frequency shift, $\theta_k$, and the estimated amplitude, $a_K$, may then be used as indices characterizing arrhythmia present in the input atrial signal.

Preferably, and as described in more detail below, the method further involves updating the template spectrum, $\phi$, using a frequency shifted version of the frequency spectrum, $q_K$, calculated for the k:th time window. The updated template spectrum, $\phi_k$, is always shifted to a fundamental frequency position, pK, which corresponds to the position of a peak found by peak detection in an exponentially averaged input spectrum, $S_K$. Additionally, and as described below, a set of parameters which describes the template spectrum may be calculated and used as further indices in the characterization and identification of the presence of arrhythmias in the input atrial signal. These are: normalized peak amplitude, $b_k$, exponential decay, $\lambda_k$, and signal-to-noise ratio, $K_k$.

In the present example only the frequency interval in the region of between 2.5 and 25 Hz is selected. This interval is chosen such that slow tachycardias, down to the lower frequency limit of about 2.5 Hz, can be represented. The upper limit of about 25 Hz is selected because possible spectral content above this is usually too weak to detect. It will be appreciated by those skilled in the art that these limits may be adjusted empirically dependent on the atrial events to be characterized.

As mentioned above, since during tachycardia the cycles are often of equal length and since for fibrillation the cycle lengths often vary rapidly in an irregular way but for short intervals, typically 1 to 2 seconds, and may also be viewed as approximately stationary during short analysis time windows a temporally isolated portion of the input atrial signal may be represented as a fundamental and a number of harmonics reflecting the shape of the waveform. A time window of in the region of 2 to 2.5 seconds is required for accurate estimation with a slowest frequency of 2.5 Hz. Another reason for this short time window is that possible small QRST residuals appear at low frequencies depending on the R-R interval and the window length. If the QRST residuals are of high amplitude or occur in a periodic manner then they may have spectral content above 2.5 Hz if using a longer window.

The following describes the method of the present invention in more detail.

All obtained ECG signals are first filtered for elimination of baseline wandering. Preferably, a spatiotemporal QRST cancellation scheme as disclosed in U.S. Pat. No. 6,305,231 is used to extract the atrial activity from the surface ECG signal. In addition to an average beat the spatiotemporal method uses average beats also from adjacent leads in order to improve the cancellation and to be able to compensate for variations in the electrical axis of the heart, otherwise causing large QRS residuals. The ventricular activity (QRS complex and T wave) is removed in the resulting residual ECG signal and thus this signal contains primarily atrial activity, i.e., P waves during sinus rhythm and f-waves during atrial fibrillation. Since the spectral content of interest in the residual ECG signal is well below 25 Hz, the residual ECG is preferably down-sampled from 1 kHz to 50 Hz. This operation considerably reduces the amount of data to be processed by the digital data processor 10.

The residual ECG signal, x(n), is, for the k:th window interval (overlapping blocks), represented by the data vector:

$$x_k = [x((k-1)L) \ldots x((k-1)L+N-1)]^T \quad (1)$$

where N is the window length and L is the distance between two consecutive windows. Each spectrum of the Short-Term Fourier Transform (STFT) is calculated as $$q_k = FW x_k \quad (2)$$

where F (K-by-N) is a K-point Non-uniform Discrete Fourier Transform (NDFT) matrix based on the frequency vector $f = [f_0 \ldots f_{K-1}]^T$ $$F = [1 e^{-j2\pi f} e^{-j2\pi f 2} \ldots e^{-j2\pi f(N-1)}] \quad (3)$$

where 1 is a column vector of length K. The diagonal entries in the diagonal matrix W (N-by-N) represent a window function (here chosen as Hamming function).

In the present embodiment of the method, the non-uniform STFT has a logarithmic frequency scale such that a doubling in frequency for all frequencies corresponds to the same number of frequency bins.

$$f_n = f_0 \cdot 10^{\frac{n}{K}} \quad n = 0 \ldots K-1 \quad (4)$$

The motivation for this is to be able to shift the harmonic pattern of one spectrum such that it matches the harmonic pattern for another spectrum with a different fundamental frequency. This is an important feature when estimating the frequency shift needed to match each new spectrum to the template spectrum. A result of the logarithmic frequency scale is that the frequency resolution for the fundamental is much higher compared to that for the harmonics.

Each spectrum $q_k$ is modeled as an amplified ($a_k$) and frequency-shifted ($\theta_k$) known template spectrum ($\phi_k$) containing a fundamental and a harmonic pattern.

$$q_k = a_k J_{\theta_k} \tilde{\phi}_k \quad (5)$$

The notation ($\tilde{\cdot}$) represents an extended vector with $\Theta$ (maximum frequency shift) extra samples in both the beginning and the end in order to allow the selection of different parts of the vector. It is assumed that the template spectrum is normalized to unit energy and has a harmonic structure such that it has a fundamental, its harmonics and a noise baseline. The extra samples can therefore be set to the same value as the noise floor. Then the adjusted template spectrum will also be approximately normalized to unit energy. There are now $2\Theta+1$ possible sets of K samples that can be selected from $\tilde{\phi}_k$. The selection is done using the shift matrix $J_\theta$ defined as $$J_{\theta_k} = [0_{K \times (\Theta + \theta_k)} I_{K \times K} 0_{K \times (\Theta - \theta_k)}] \quad (6)$$

which selects K samples from $K+2\Theta$. The zero matrices thus throw away energy from the template spectrum. This energy is assumed to be in the noise baseline and approximately the same energy is introduced on the other side of the spectrum.

Least-squares estimation of the frequency shift and amplitude is performed using the cost function $$J(\theta_k, a_k) = (q_k - a_k J_{\theta_k} \tilde{\phi}_k)^T (q_k - a_k J_{\theta_k} \tilde{\phi}_k) \quad (7)$$

which can be written $$J(\theta_k, a_k) = q_k^T q_k - 2 a_k q_k J_{\theta_k} \tilde{\phi}_k + a_k^2 (J_{\theta_k} \tilde{\phi}_k)^T (J_{\theta_k} \tilde{\phi}_k) \quad (8)$$

where $(J_{\theta_k} \tilde{\phi}_k)^T (J_\theta \tilde{\phi}_k) \approx 1$ yielding $$J(\theta_k, a_k) \approx q_k^T q_k - 2 a_k q_k J_{\theta_k} \tilde{\phi}_k + a_k^2 \quad (9)$$

The minimization with respect to the frequency shift, $\theta_k$, is now independent of the amplitude, $a_k$, and performed by maximizing the second term of 9 using a grid search of $\theta$ in the interval $[-\Theta, \Theta]$ in order to find the optimum frequency shift, $\hat{\theta}_k$, $$\hat{\theta}_k = \underset{\theta_k}{\mathrm{argmax}} (J_{\theta_k} \tilde{\phi}_k)^T q_k \quad (10)$$

When the frequency shift is estimated, the amplitude, $\hat{a}_K$, is given as the inner product $$\hat{a}_k = q_k^T J_{\hat{\theta}_k} \tilde{\phi}_k \quad (11)$$

A measure of how well the model in (5) fits the current spectrum, $q_K$ is the model error, $e_k$, between the frequency-shifted and scaled template spectrum and each spectrum is determined as $$e_k = q_k - \hat{a}_k J_{\hat{\theta}_k} \tilde{\phi}_k \quad (12)$$

The model error, $e_k$, is used for detection of temporally isolated portions of the atrial signal which are not well represented by the model assumptions. The model error is not normalized to the signal amplitude and is thus severely influenced by it. An alternative model error measure is then $$\bar{e}_k = \frac{e_k}{a_k} \quad (13)$$

This measure may be used to increase a template spectrum adaptation gain, $\alpha_k$, (see below) in order to faster track a new signal pattern.

The above described parameter estimation requires that the template spectrum is given. A desired feature is to be able to adapt to the template spectrum in the data record and to allow adaptation to changes in the waveform characteristics of the signal that may occur later. The present method is therefore preferably implemented in an adaptive fashion such that the template spectrum is slowly updated for every new spectrum. However, an initial template spectrum needs to be selected. The initial template spectrum must contain a major peak towards which all the spectra are shifted. After the frequency shift, $\hat{\theta}_k$, and amplitude, $\hat{a}_K$, estimation is performed for each new spectrum as described above, the template spectrum $\phi$ is updated by averaging with each new spectrum, shifted such that it has it, peak at the fundamental position in the template spectrum, according to $$\hat{\phi}_{k+1} = \frac{(1 - \alpha_k) \hat{\phi}_k + \alpha_k \frac{J_{-\hat{\theta}_k} \tilde{q}_k}{\|J_{-\hat{\theta}_k} \tilde{q}_k\|}}{\left\| (1 - \alpha_k) \hat{\phi}_k + \alpha_k \frac{J_{-\hat{\theta}_k} \tilde{q}_k}{\|J_{-\hat{\theta}_k} \tilde{q}_k\|} \right\|} \quad (14)$$

where $\alpha_k$ is the template spectrum adaptation gain. The adaptation gain, $\alpha_k$, is altered by a signal reliability, $z_k$; thus $\alpha = \alpha(z_k)$. The fiducial point and beat class vectors from the QRST cancellation process is used in order to determine the degree of reliability of each new spectrum. Ectopic beats, especially those with unknown morphology, i.e., with rarely occurring beat class, typically indicates a low reliability. A low reliability in the spectrum suggests that the present spectrum not should be adapted into the template spectrum. The fiducial point and beat class vectors thus serves as a measure of what information that is useful as input to the algorithm. The signal reliability $z_k$, is set to 1 for signal intervals that are reliable and to zero otherwise. The signal reliability is used to adapt the template spectrum adaptation gain $\alpha_k$. For intervals with signal reliability zero $\alpha_k$ also is set to zero.

A property in the frequency shift estimation is that there is a maximum shift in each direction (to save computational effort). It is obviously most effective if the shift interval is centred around the average atrial frequency. Depending on where average atrial frequency is located compared to the selected initial fundamental frequency position the fundamental position in the template spectrum may need to be adjusted to optimally use the shift interval. The shift interval can then be decreased after adjustment of the fundamental position in the template spectrum to the average atrial frequency. Therefore the initial fundamental position, $p_0$, is adapted for each new spectrum. At time k, the frequency shift vector, $\theta_k$ is relative to the fundamental position $p_k$. For each new signal window, an exponentially averaged spectrum, $S_k$ is updated as $$S_k = (1-\nu)S_{k-1} + \nu q_k \quad (15)$$

where $S_0$ is the first spectrum and $\nu$ and adaptation gain. The fundamental position, $\hat{p}_k$, is updated according to $$\hat{p}_{k+1} = \arg\max S_k \quad (16)$$

The fundamental position estimate is then compared to the last estimate $p_k$ $$\epsilon_k = \hat{p}_{k+1} - \hat{p}_k \quad (17)$$

and if a discrepancy is detected, the template spectrum, $\phi_{k+1}$, needs to be adjusted since it should have the fundamental peak at $p_{k+1}$. This adjustment is made according to the equation:

$$\hat{\phi}_{k+1} = J_{\frac{\epsilon_k}{|\epsilon_k|}} \hat{\phi}_{k+1} \quad (18)$$

The template spectrum, $\phi_k$, contains a fundamental peak and a number of harmonics. The fundamental peak and all harmonics are for the logarithmic frequency scale located at the following frequency bins respectively $$g = [g(0)\ g(1)\ \cdots\ g(q)]^T \quad (19)$$
$$= p_k + K \cdot [0\ \lfloor\log_{10}2\rfloor\ \cdots\ \lfloor\log_{10}(m+1)\rfloor]^T$$

where the notation $\lfloor \ldots \rfloor$ indicates rounding to the closest integer, and m is the number of harmonics below 20 Hz. For every k, the template spectrum, $\phi_k$, before it is updated, is parameterised using the model $$\phi_k(g(i)) = b_k e^{-\gamma k^i} i = 0, 1, \ldots, m \quad (20)$$

where g(i) is the above-described resampling function. The model in equation 20 can be rewritten $$\ln\phi_k(g(i)) = \ln b_k - \gamma k^i i = 0, 1, 2, \ldots m \quad (21)$$

Least-squares estimation is employed using the cost function $$J(\ln b_k, \lambda_k) = \sum_{i=0}^{m}(\ln\phi_k(g(i)) - (\ln b_k - \gamma_k^i))^2 \quad (22)$$

Setting the derivatives with respect to $\ln b_k$ and $\lambda_k$ to zero $$\frac{\delta J(\ln b_k, \lambda_k)}{\delta(\ln b_k)} = \sum_{i=0}^{m}(-2\ln\phi_k(g(i)) + 2\ln b_k - 2i\lambda_k) = 0 \quad (23)$$

$$\frac{\delta J(\ln b_k, \lambda_k)}{\delta\lambda_k} = \sum_{i=0}^{m}(2i\ln\phi_k(g(i)) - 2i\ln b_k + 2i^2\lambda_k) = 0 \quad (24)$$

yields the following LS estimators of the normalised peak amplitude and the exponential decay $$\hat{b}_k = e^{\frac{2(2N-1)}{M(M+1)}\sum_{i=0}^{m}\ln\phi_k(g(i)) - \frac{6}{M(M+1)}\sum_{i=0}^{m}i\ln\phi_k(g(i))} \quad (25)$$

$$-\hat{\gamma}_k = \frac{6}{M(M+1)}\sum_{i=0}^{m}\ln\phi_k(g(i)) - \frac{12}{M(M^2-1)}\sum_{i=0}^{m}i\ln\phi_k(g(i)) \quad (26)$$

where M=m+1. A more detailed summary of which signal waveforms that can be represented by this model is provided in the discussion related to FIG. 2 below.

Another useful measure is $\kappa_k$, which is used to determine whether the present harmonic pattern is valid. This measure is defined as $$\kappa_k = \frac{\phi_k(p_k) + \phi_k(p_k + \lfloor\log_{10}2\rfloor)}{2\phi_k(p_k + \lfloor\log_{10}1.5\rfloor)} \quad (27)$$

and measures to relation between the signal amplitude (average amplitude of the fundamental and the first harmonic) and the noise level in the middle between the two peaks. This can be viewed as a signal-to-noise ratio.

Figure 2:
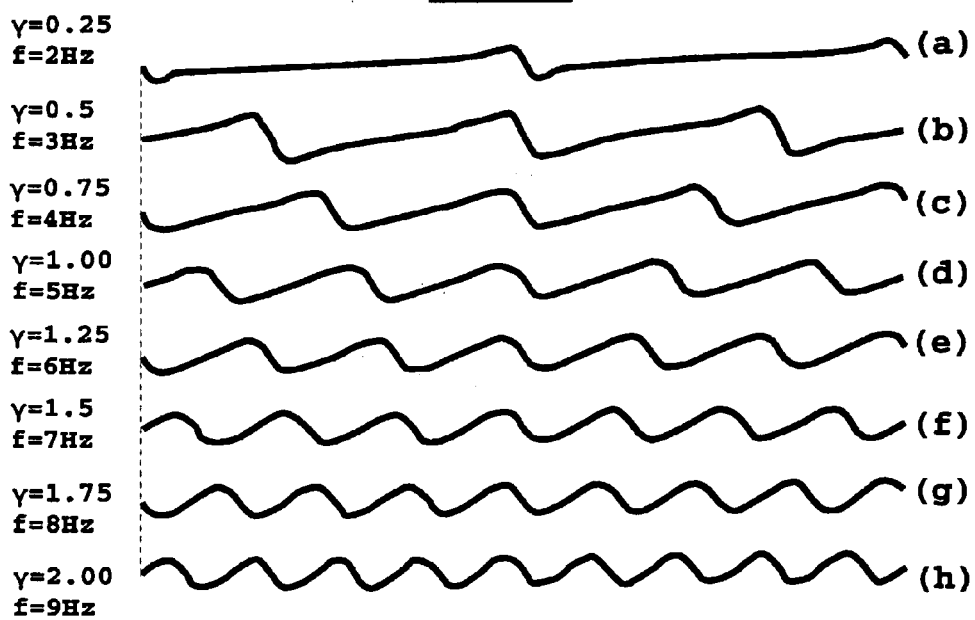
FIG. 2 illustrates waveforms capable of being represented by the exponential decay model employed in the method of the present invention.

Considering now FIG. 2, in order to be able to differentiate different types atrial signals a representative parameterisation is necessary. According to the above described exemplary embodiment of the method according to the present invention the template spectrum is parameterized into two parameters of which the exponential decay, $\gamma_k$, is the one that is important for the shape. The fundamental peak amplitude in the normalised template spectrum, $b_k$, quantifies how discrete the signal components in the spectrum are. A low value indicates that the spectrum not only consists of a few discrete signal components, but also a relatively high noise baseline. The suggested model can represent a large number of different waveforms (a)–(h) as illustrated in FIG. 2 in which both the exponential decay $\gamma_k$ and the frequency, f, increase from (a) to (h) with (a) $\gamma$=0.25,f=2 Hz; (b) $\gamma$=0.5,f=3 Hz; (c) $\gamma$=0.75,f=4 Hz; (d) $\gamma$=1,f=5 Hz; (e) $\gamma$=1.25,f=6 Hz; (f) $\gamma$=1.5,f=7 Hz; (g) $\gamma$=1.75, f=8 Hz; and (h) $\gamma$=2,f=9 Hz;. As can be seen, the higher exponential decay, $\gamma$, the more sinusoidal the waveform. With this model it is not possible to fully represent the characteristic saw tooth shape of organised atrial fibrillation waves. Therefore, it may be useful to complement this model with other models such as one with harmonic amplitudes described by $2^{-i}$ for the i:th harmonic. The model with smallest error, $e_k$ or $\bar{e}_k$, should then be used.

The application of an apparatus which is functionally similar to that of FIG. 1 to the analysis of surface ECG traces will now be exemplified.

Figure 3:
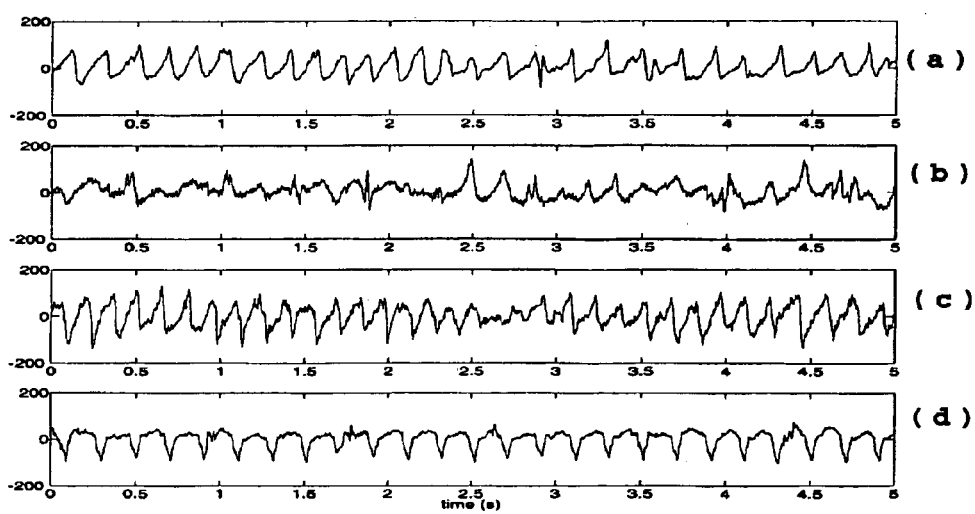
FIG. 3 illustrates 5 seconds from each of four ECG signals after QRST cancellation.

Five seconds of time ECG signals from four different patients (a)–9d) in which the ventricular activity has been cancelled are shown in FIG. 3. Decomposed time-frequency distributions for similar time domain signals are presented in FIGS. 4a–4d. For all analysis the following parameter settings were used: Both the signal window length and the number of NDFT points were set to N=K =128 with a signal window distance of L=50. The frequency vector was created with $f_0$=2.5 Hz. The initial fundamental position was $p_0$=42 corresponding to around 5.3 Hz. The maximum shift was set to $\Theta$=25 after finding the correct average fundamental position such that the shift interval is centred around the average atrial frequency. The template spectrum was initiated with $$\phi_0(i) = \begin{cases} 1 & i = p_0 \\ 0.01 & \text{otherwise} \end{cases} \quad (28)$$

The adaptation gains were set to $\alpha$=0.1 and $\nu$=0.05.

If the first harmonic happens to have larger amplitude than the fundamental the fundamental position corresponding to the found peak was always tested in the average peak location estimation. If there exists a peak with >70% of the amplitude compared to the found peak the lower peak is chosen as the estimate. If a signal interval contain a beat from a beat class that have occurred less than six times then the signal reliability, $z_k$, was set to zero for that interval.

In each of FIGS. 4a–4d the section (i) shows the last template spectrum, $\phi_{58}$, (solid curve) with, for comparison, the power spectrum (FAF [frequency analysed fibrillation, after M Holm et. al. "Non-Invasive Assessment of Atrial Refractoriness During Atrial Fibrillation In Man—Introducing, Validating and Illustrating a New ECG Method", Cardiovascular Research, Vol 38, pp. 69–81, 1998], dotted curve) as well as the estimated exponential model(dot/dash curve); (ii) the frequency trend and the averaged fundamental position (dotted curve) is shown; and (iii) presents the average values of the amplitude, $a_k$, signal-to-noise ratio, $\kappa_k$, normalized amplitude, $b_k$, normalized model error, $\bar{e}_k$, model error, $e_k$, exponential decay, $\gamma_k$, and the signal reliability, $z_k$ (note that the value zero represents best reliability), for the last 20 seconds.

Figure 4A:
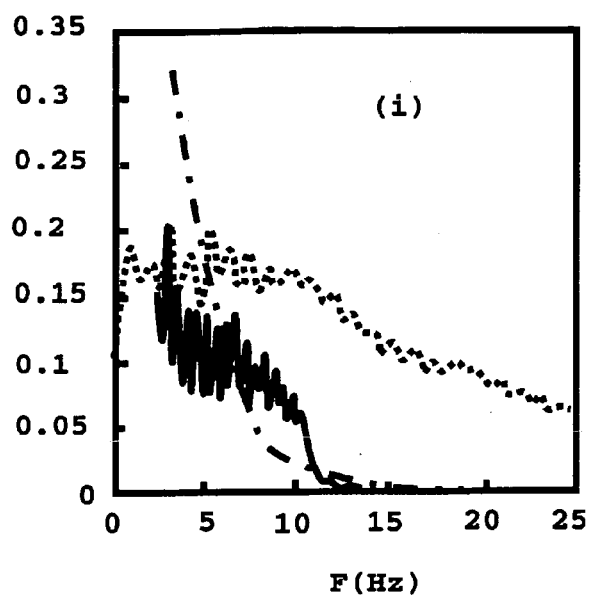
FIGS. 4a, 4b, 4c and 4d illustrate decomposition according to the present method of 1 minute of signals similar to those of FIG. 3 containing different arrhythmia events.
Figure 4A:
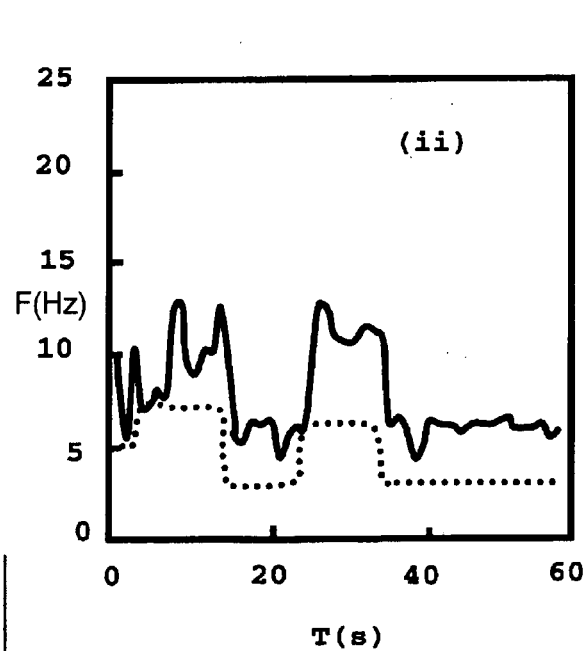
Figure 4B:
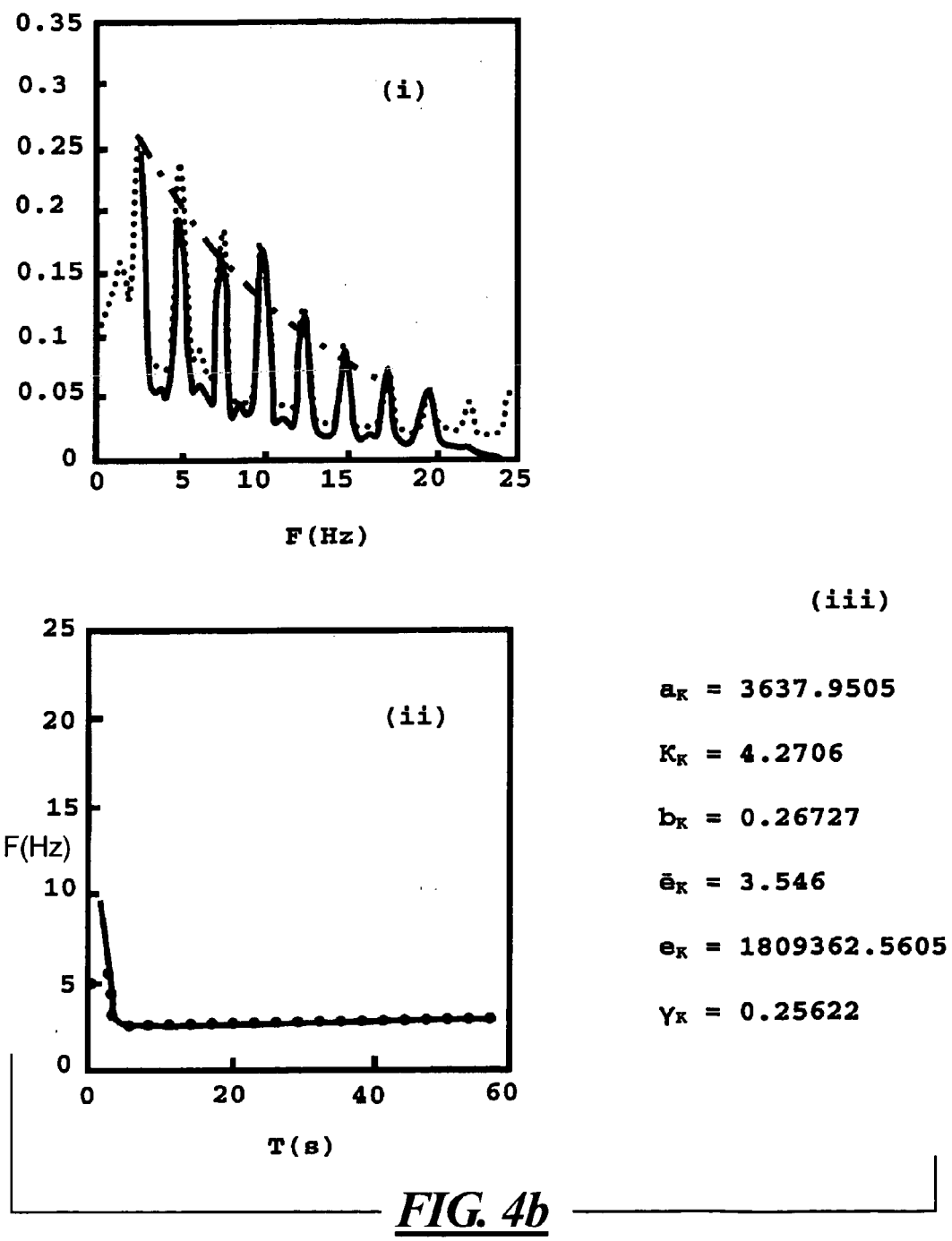
Figure 4C:
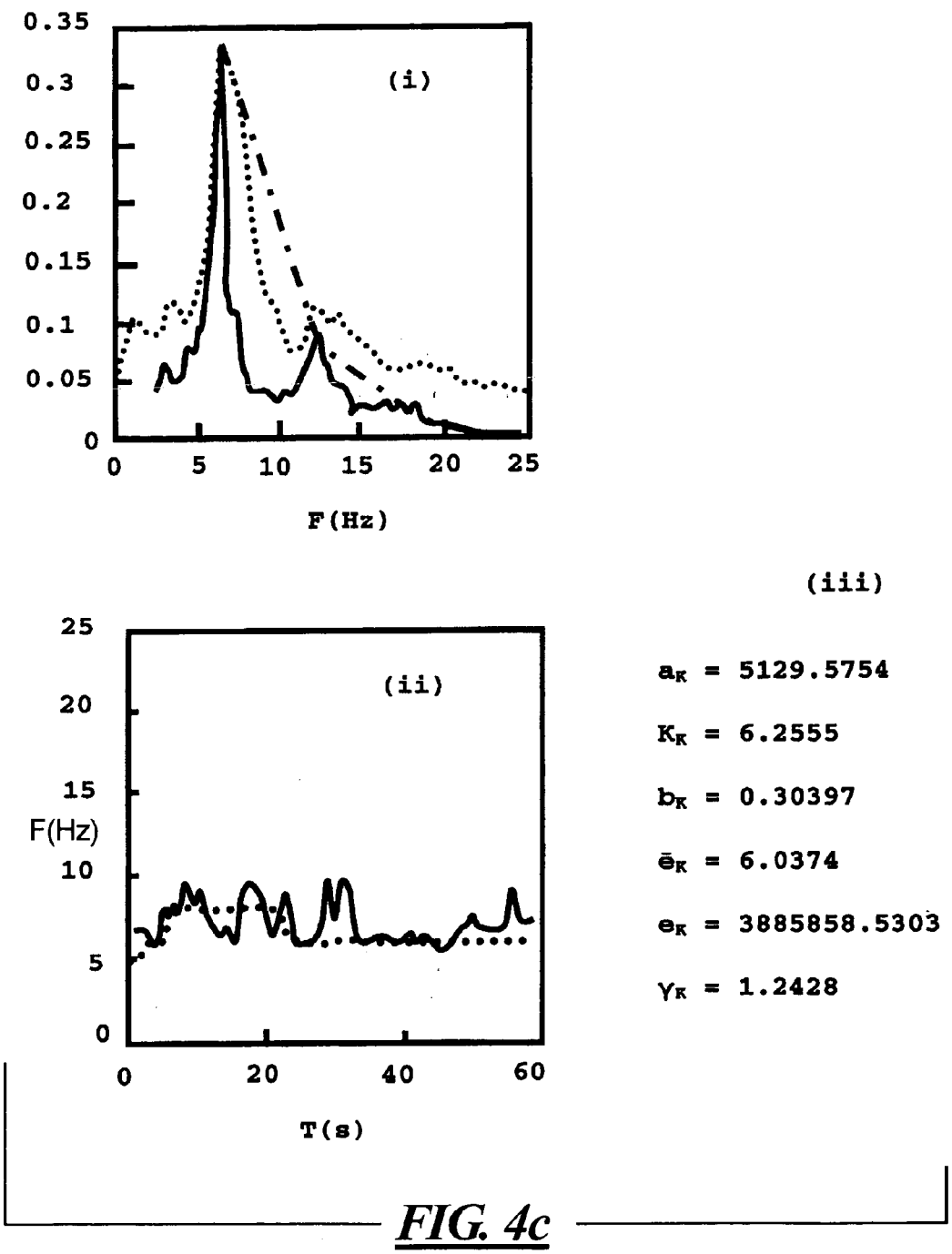
Figure 4D:
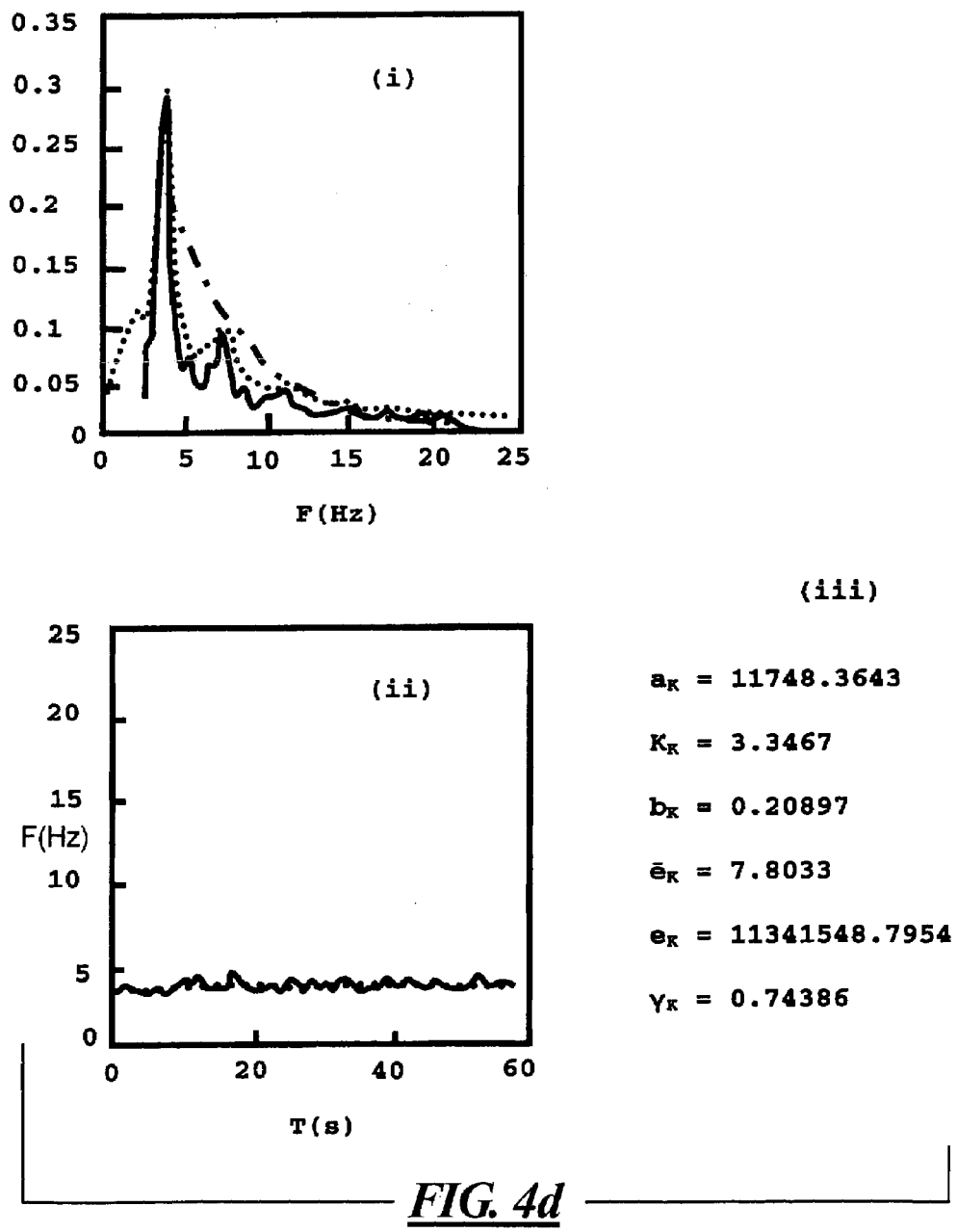

The examples of FIGS. 4a, 4b and 4c illustrate the performance of the apparatus operating according to the method of the present invention when analysing ECG spectra similar to those of FIG. 3 for cases of fibrillation, tachycardia, sinus rhythm and very slow fibrillation/flutter. In FIG. 4a a slow tachycardia with a fundamental frequency of around 2.5 Hz is shown. The frequency trend in this case is constant and seven harmonics can be seen in the template spectrum. FIG. 4b shows sinus rhythm, that is P-waves, with a fundamental below the allowed 2.5 Hz limit. The window length of around 2.5 seconds (corresponding to L=50) is also too short to analyse these signals. Since the spectral shifting does not work when the fundamental is below 2.5 Hz then the template spectrum is not discrete. The relationship between the signal amplitude and the signal-to-noise ratio is calculated to be 1.16 which is too low since a value of at least 2 is required. FIGS. 4c and 4d illustrate two cases of atrial fibrillation, one (c) with a fundamental, around 7 Hz and one (d) with a fundamental around 3 Hz with, in both cases at least one clearly discernible harmonic.

Similar analysis for a number of known arrhythmias is made to provide the database 24 with which the event classifier 22 can operate to classify the arrhythmia event. The signal is classified in the event classifier 22 as a tachycardia if the variance of the frequency is less than 0.1 Hz and as fibrillation/flutter if above. A frequency of above 4.5 Hz is regarded as indicating fibrillation while a frequency below this is regarded as signifying flutter.

A comparison of the calculated amplitude with database values classifies the arrhythmia as flutter when large amplitudes (in the present embodiment) above 7000 with tachycardias and fibrillation having similar amplitudes, much less than that indicating flutter. Calculated exponential decays, $\gamma$, are used by the event classifier 22 to classify a signal as a tachycardia if between 0.2 and 0.65; as flutter from 0.64 to 0.8 and as fibrillation above 0.8 to around 2.0.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computer-readable medium encoded with data and being loadable in a digital data processing system for deriving indices characterizing atrial arrhythmias, said data programming said digital signal processing system to:
    acquire a digital representation of a time-domain electrical signal originating from atria of a heart;
    temporally isolate a portion of the digital representation of the time-domain signal within a variable location time window;
    frequency analyze the temporally isolated portion to obtain a frequency spectrum having a fundamental frequency peak and at least one harmonic thereof;
    compare the obtained frequency spectrum with a template frequency spectrum having a template fundamental frequency peak and at least one template harmonic thereof to determine a frequency shift value and an amplitude value that optimize a correlation between the obtained frequency spectrum and the template frequency spectrum; and
    emit an output representing the frequency shift value and the amplitude value as respective indices characterizing atrial arrhythmias in said electrical signal.

2. A computer-readable medium as claimed in claim 1 wherein said data further program the digital signal processing system to:
    adapt the template frequency spectrum by selective averaging with the obtained frequency spectrum frequency shifted to place the fundamental frequency peak coincident with the template fundamental frequency peak.

3. A computer-readable medium as claimed in claim 2 wherein said data further program the digital signal processing system to:
    generate an averaged frequency spectrum derived from the frequency spectrum and previous frequency spectra obtained from previous temporally isolated portions with differing timewindow locations within the digital representation of the time-domain signal; and
    adapt the template frequency spectrum by shifting the spectrum to make the template fundamental frequency coincide with a fundamental peak position within the averaged frequency spectrum.

4. A computer-readable medium as claimed in claim 2 wherein said data further program the digital signal processing system to:
    analyze the template frequency spectrum before adaptation to determine values for at least one parameter selected from the group, consisting of fundamental frequency peak amplitude, exponential decay, and signal-to-noise ratio.

5. A digital data processing system for determining indices characterizing atrial arrhythmias comprising:
- a storage unit for receiving and holding, for subsequent data processing a digital representation of a time-domain electrical signal originating from atria of a heart;
- a time window generator operably connected to the storage unit for temporally isolating a portion of the held digital representation within a moveable time window;
- a spectrum analyzer which frequency analyzes the temporally isolated portion to obtain a frequency spectrum having a fundamental frequency peak and one or more harmonics thereof; and
- a comparator for comparing the obtained frequency spectrum with a template frequency spectrum having a template fundamental frequency peak and at least one template harmonic thereof to determine a frequency shift value and an amplitude value that optimize a correlation between the obtained frequency spectrum, and the template frequency spectrum, and for providing an output representing the frequency shift value and the amplitude value as respective indices characterizing atrial arrhythmias in said electrical signal.

6. A digital data processing system as claimed in claim 5 wherein the time window generator varies the location of the time window to temporally isolate a plurality of overlapping portions of the held digital representation, each for analysis by the spectrum analyzer to provide a corresponding plurality of frequency spectra, and further comprising a spectrum generator which modifies the template frequency spectrum dependent on at least one of the plurality of frequency spectra.

7. A digital data processing system as claimed in claim 6 further comprising:
- an analyzer which analyzes the template frequency spectrum before modification to determine a value of at least one of a fundamental frequency peak amplitude, an exponential decay, and a signal-to-noise ratio characterizing the template and which provides the at least one value as an output; and
- an event classifier which receives the outputs from the analyzer and the comparator and which provides an output representing a classification of an atrial arrhythmia present in the acquired digital representation of the time-domain electrical signal.

* * * * *